(12) United States Patent
Jenn

(10) Patent No.: US 10,064,905 B1
(45) Date of Patent: Sep. 4, 2018

(54) PHARMACEUTICAL PREPARATION

(71) Applicant: Dennis M. Jenn, South Jordan, UT (US)

(72) Inventor: Dennis M. Jenn, South Jordan, UT (US)

(73) Assignee: Ilysm, LLC, Murray, UT (US)

( * ) Notice: Subject to any disclaimer, the term of this patent is extended or adjusted under 35 U.S.C. 154(b) by 33 days.

(21) Appl. No.: 14/538,527

(22) Filed: Nov. 11, 2014

Related U.S. Application Data

(60) Provisional application No. 61/902,501, filed on Nov. 11, 2013.

(51) Int. Cl.
| | |
|---|---|
| *A61K 36/00* | (2006.01) |
| *A61K 36/185* | (2006.01) |
| *A61K 9/00* | (2006.01) |
| *A61K 31/352* | (2006.01) |
| *A61K 31/05* | (2006.01) |
| *A23L 1/30* | (2006.01) |
| *A21D 13/08* | (2006.01) |
| *A23C 15/12* | (2006.01) |

(52) U.S. Cl.
CPC ............ *A61K 36/185* (2013.01); *A21D 13/08* (2013.01); *A23C 15/12* (2013.01); *A23L 1/3002* (2013.01); *A61K 9/007* (2013.01); *A61K 9/0034* (2013.01); *A61K 31/05* (2013.01); *A61K 31/352* (2013.01); *A23V 2002/00* (2013.01)

(58) Field of Classification Search
CPC ...................................................... A61K 36/00
USPC ....................................................... 424/725
See application file for complete search history.

(56) References Cited

U.S. PATENT DOCUMENTS 8,603,515 B2 * 12/2013 Whittle .................. A61K 31/05
424/435

FOREIGN PATENT DOCUMENTS

WO  WO 2007/002125   *  1/2007

OTHER PUBLICATIONS

Hemp Protein, 14 pages, 2016.*
Shmist et al., Molecular and Cellular Biochemistry 283: 75-83, 2006.*
IACM-Bulletin of Feb. 19, 2006, 2 pages.*
"Sex and Weed—Does Marijuana Enhance Sex or Destroy it?", http://www.killerweednovel.com/sex-and-weed-does-marijuana-enhance-sex-or-destroy-it/, Accessed Mar. 9, 2015.

* cited by examiner

*Primary Examiner* — Michael V Meller
(74) *Attorney, Agent, or Firm* — Workman Nydegger

(57) ABSTRACT

Pharmaceutical preparations include at least one component that enhances sexual response and at least one other compound that enhances sexual sensitivity and pleasure. The component that enhances sexual response enhances blood flow to the genital region. Examples include compounds that dilate blood vessels, such as compounds that increase the amount of nitric oxide (NO) in the blood. The component that enhances sexual sensitivity and pleasure includes one or more cannabinoid compounds from the plant genus *Cannabis*. Examples include tetrahydrocannabinol (THC), the main psychoactive constituent of *Cannabis*, and cannabidiol (CBD), which is less or non-psychoactive and modulates THC activity. The ratio of THC/CBD can be selected depending on age, gender, physical health, and/or psychological condition of the user.

20 Claims, No Drawings

PHARMACEUTICAL PREPARATION

CROSS REFERENCE TO RELATED APPLICATION

This Application claims the benefit of U.S. Prov. App. Ser. No. 61/902,501, filed Nov. 11, 2013, the disclosure of which is incorporated herein in its entirety.

BACKGROUND OF THE INVENTION

1. Field of the Invention

The invention is in the field of pharmaceutical preparations, particularly those for sexual enhancement in men, women, the disabled, and the aged.

2. Relevant Technology

There are a variety of health issues that can impact the ability or desire to engage in intimate sexual relations, which form a healthy part of adult relationships. These include sexual dysfunction in men and women and a loss of sensitivity and pleasure. The inability to perform and/or lack of desire to engage in sexual relations can detrimentally impact a relationship and can lead to divorce, breakup, or long-term boredom. It can lead to loss of self-esteem or even mental illness.

Men are more likely than women to have threshold desire to have sex, which is both a physical and psychological need, and are therefore more likely to initiate sex with a partner. When a man is extremely stressed, anxious or insecure, however, his ability to perform can also be inhibited physically (temporary erectile dysfunction). Older or sick mean can suffer chronic erectile dysfunction ("ED"), which can be completely incapacitating relative to ability to perform. Particularly as men age and/or if suffering from chronic illness, can experience lack of threshold desire, loss of sensitivity, loss of pleasure and/or difficulty in climaxing. At the opposite end of the spectrum is premature ejaculation which, while not preventing performance, can severely curtail duration and satisfaction for both participants.

In women, sexual dysfunction is more complex and difficult to define but can involve lack of threshold desire, loss of sensitivity, loss of pleasure and/or inability to climax. Emotional and psychological sexual dysfunction is more common among women, which is probably the main reason many women never achieve orgasm during sex. They get stuck in a rut emotionally and mentally. There are many studies that show that women commonly have very real insecurities about body image and carry their stresses and anxieties of life with them into the bedroom. These insecurities and stresses greatly impact the mood-factor (emotional and psychological state) and inhibit physiological arousal, such as decreased blood flow to the clitoris and labia, often making orgasm unattainable.

Compared to men, women have more complex emotions that can be barriers to threshold desire. Women are more sensitive sexually to their insecurities, stresses, and anxieties than men. Books and commentators have been known to say: "sex is much more emotional for women than men." Also, men often view sex as a way to release and reduce stress and tension. In contrast, women often identify sex with increased stress and anxiety, particularly women who both work outside the home and raise children. Examples of hypothetical stresses include: "I'm not in the mood." "I'm stressed or tired from work, the kids, play dates, managing the household, dirty dishes." "Really? We're doing this now, etc.?" So, sex can becomes another item on an already stressful checklist. Example of hypothetical anxieties include: "I'm not in the mood." "I think I've put on a few pounds." "My butt doesn't look good." "I feel bloated and hormonal." "Will I be able to perform for my partner, act sufficiently interested, be interested, etc.?"

While there are drugs (e.g., Viagra®, Cialis® and Levitra®) that can remedy ED and permit men to perform sexually, they generally do not restore lost sensitivity, diminished enjoyment, or difficulty in climaxing. Such drugs are generally ineffective for women because they do not adequately address issues involving lack of threshold desire, loss of sensitivity, loss of pleasure or inability to climax (i.e., because they do virtually nothing to address powerful psychological forces affecting women).

In fact, the main reason physiological enhancers for women on the market today do not work is because none address the mood-factor. Unlike men, who feel buildup of semen and equate it with sexual tension and need to find sexual release, the trigger for women to desire sex is typically not physical but psychological and strongly correlated with mood and self-image. Their emotional and psychological state can actually dictate physiological response, arousal and performance significantly more than in men. And while men are notorious finishers during sex, women are not so prone (50% reportedly never achieving orgasm during sex). This is generally not due to a lack of physical stimulation but rather emotional barriers or inhibitions. Only enhancing the physiological response in women cannot address an inability to reach climax.

Many of the foregoing problems are particularly acute in men and women who suffer from physical ailments and/or age-related conditions that cause sexual dysfunction and/or lack of desire and enjoyment. Again, it must be emphasized that performance does not necessarily coincide with normal enjoyment of sexual relations. Drugs that only address lack of performance but fail to address diminished desire, sensitivity and pleasure are incomplete solutions.

While there are herbal supplements that purport to address some or all of the foregoing issues, there remains a long-felt but unmet need to find compositions that effectively and reliably addresses diminished performance while also increasing desire, sensitivity and enjoyment.

SUMMARY

The present invention relates to pharmaceutical preparations and related methods of manufacture and use for enhancing various aspects of sexual activity. To accomplish these results the pharmaceutical preparations include a combination of: (1) one or more cannabinoid compounds derived from the plant genus *Cannabis*, which are included in an amount and/or in a ratio so as to enhance sexual pleasure (e.g., threshold desire, sensitivity and/or enjoyment); and (2) one or more compounds that enhance blood flow to the genital region in order to enhance sexual response (e.g., ability to perform and/or time to arousal). The combination results in increased ability to perform and enjoyment of intimate sexual activities by men and women.

According to several embodiments, the pharmaceutical preparations can be delivered in a manner so that the time of enhanced sexual response and sexual pleasure coincide or complement each other (i.e., so that both are present at the same time at least some of the time). Methods of delivery include oral delivery, topical delivery, injection, inhalation, or combinations thereof. Advantageously, the components of the pharmaceutical preparations can be delivered together in a single mode of delivery for simplicity and proper dosage (e.g., in a combined oral preparation or a topical preparation). Alternatively, the components of the pharmaceutical preparations can be pre-packaged in a kit and delivered individually, whether simultaneously or sequentially.

According to several embodiments, the one or more cannabinoid compounds derived from the plant genus *Cannabis* include at least two cannabinoid compounds that are included in amounts and/or ratios in order to address a particular condition being treated. By way of example, it has been found that persons (men or women) suffering from lack of threshold desire, sensitivity, pleasure and/or ability to climax can benefit from preparations that have a relatively higher quantity or ratio of tetrahydrocannabinol (THC) as compared to cannabidiol (CBD) (e.g., more than 2:1 THC/CBD). Alternatively, persons suffering from premature ejaculation (men) or who are prone to nervousness or anxiety when engaging in sexual activity (men or women) can benefit from preparations that have a relatively lower quantity THC/CBD ratio (e.g., less than 0.5:1 THC/CBD). Persons with normal sexual response can benefit from an intermediate THC/CBD ratio (e.g., between 0.5:1 to 2:1 THC/CBD).

As discussed above, women can have very real insecurities about body image and carry stresses and anxieties into the bedroom. Similarly, when a man is extremely stressed, anxious or insecure, his ability to perform sexually can also be inhibited physically. Insecurities and stresses can greatly impact emotional and psychological state and inhibit physiological arousal, often making sex impossible for the man and/or orgasm unattainable for the woman. However, by addressing both the mood-factor (emotional and psychological state) and bloodflow to the genitalia, physical arousal occurs easier and more naturally, which permits awareness and focus to shift to sensuality, sexual sensitivity, and sexual stimulation, enhancing sexual pleasure for both men and women, and promoting fast orgasms and sometimes multiple orgasms.

DETAILED DESCRIPTION OF THE PREFERRED EMBODIMENTS

Disclosed herein are pharmaceutical preparations that include at least one compound that enhances sexual pleasure and at least one other compound that enhances sexual response. Also disclosed are methods of manufacturing and using such pharmaceutical preparations.

The term "sexual pleasure" can include a variety of physiological and/or psychological aspects or conditions that affect the amount of enjoyment of sexual activity. Examples include, but are not limited to, threshold desire to commence sexual activity, physical sensitivity during sexual activity, psychological pleasure or awareness during sexual activity, ability to reach climax, amount of pleasure leading up to climax, quality of climax, duration of climax, and the like.

The term "sexual response" can include a variety of physiological and/or psychological aspects that affect the ability to perform sexual activities. In men, the most common condition is the inability to achieve or maintain an erection. In women, conditions that inhibit sexual response are more varied and complex but include, for example, inability or delay in becoming aroused while being kissed or touched in erogenous zones. In many cases such inability can be more psychological rather than physiological.

According to several embodiment, the one or more compound that enhance sexual pleasure ("pleasure-enhancing component") include one or more cannabinoid compounds from the plant genus *Cannabis*. Examples of cannabinoid compounds include tetrahydrocannabinol ("THC"), which is a subgenus of several different isomers having different chiral centers and is the main psychoactive constituent of *Cannabis*; cannabidiol ("CBD"), which is less or perhaps even non-psychoactive but may block certain effects of THC in the nervous system, cannabinol ("CBN"), tetrahydrocannabivarin ("THCV"), and cannabigerol ("CBG"). Examples of synthesized cannabinoids include dronabinol (Marionol) (a pure isomer of THC, (−)-trans-Δ9-tetrahydrocannabinol, which is the main isomer found in *cannabis*) and nabilone (a synthetic racemic mixture consisting of the (S,S) and the (R,R) isomers of THC).

Without being bound to any particular theory, it is postulated that pharmaceutical preparations that have higher quantities of THC have a more excitatory effect on the central nervous system while pharmaceutical preparations that have lower quantities of THC and/or higher quantities of CBD can have a more calming effect. Selecting the optimal combination of excitatory and calming effects can be advantageous in treating a particular sexual dysfunction.

Accordingly, optimal results can be achieved when the pharmaceutical preparation includes at least two cannabinoid compounds that are included in amounts and/or ratios in order to address a particular condition being treated. It should be understood that *Cannabis* plants typically have dozens of cannabinoids and that the THC/CBD ratios expressed herein may work best when a substantially quantity (e.g., most or all) of the cannabinoid compounds found in *Cannabis* plants are included. In fact, the THC/CBD ratios may, in at least some cases, be a proxy for the ratio of other cannabinoid compounds found in a particular *Cannabis* species.

By way of illustration, it has been found that persons (men or women) suffering from lack of threshold desire, sensitivity, pleasure and/or ability to climax can benefit from preparations that have a relatively higher quantity or ratio of tetrahydrocannabinol (THC) as compared to cannabidiol (CBD). Such preparations may be euphemistically called "high excitement preparations" (or "amplifying preparations").

Alternatively, persons suffering from premature ejaculation (men) or who are prone to nervousness or anxiety when engaging in sexual activity (men or women) can benefit from preparations that have a relatively lower quantity or ratio of THC as compared to CBD (or higher ratio of CBD to THC). Such preparations may be euphemistically called "calming preparations" (or "stabilizing preparations").

In yet other cases, people who do not suffer from any particular condition but nevertheless wish to enhance sexual experience can benefit from preparations that have a balanced quantity or ratio of THC as compared to CBD. Such preparations may be euphemistically called "intermediate preparations" (or "balanced preparations").

According to several embodiments, the quantity of THC in amplifying preparations can be in a range of about 50 to 500 mg per dose, or about 75 to 400 mg per dose, or about 100 to 300 mg per dose. To complement the THC, the quantity of CBD in amplifying preparations can be in a range of about 10 to 250 mg per dose, or about 15 to 200 mg per dose, or about 25 to 150 mg per dose. The ratio of THC to CDB in amplifying preparations can be at least about 2:1

THC/CBD, or in a range of about 2:1 to 25:1 THC/CBD, or about 3:1 to 20:1 THC/CBD, or about 4:1 to about 15:1 THC/CBD.

According to several embodiments, the quantity of THC in stabilizing preparations can be in a range of about 10 to 250 mg per dose, or about 15 to 200 mg per dose, or about 25 to 150 mg per dose. To complement the THC, the quantity of CBD in stabilizing preparations can be in a range of about 50 to 500 mg per dose, or about 75 to 400 mg per dose, or about 100 to 300 mg per dose. The ratio of THC to CDB in stabilizing preparations can be less than or equal to about 0.5:1 THC/CBD. Stated another way, the ratio of CBD to THC can be at least about 2:1 CBD/THC, or in a range of about 0.5:1 to 25:1 CBD/THC, or about 3:1 to 20:1 CBD/THC, or about 4:1 to about 15:1 CBD/THC.

According to several embodiments, the quantity of THC in balanced preparations can be in a range of about 25 to 400 mg per dose, or about 50 to 300 mg per dose, or about 75 to 250 mg per dose. To complement the THC, the quantity of CBD in balanced preparations can be in a range of 25 to 400 mg per dose, or about 50 to 300 mg per dose, or about 75 to 250 mg per dose. The ratio of THC to CDB in balanced preparations can be in a range of about 0.1:1 to 10:1 THC/CBD, or about 0.25:1 to 5:1 THC/CBD, or about 0.5:1 to about 2:1 THC/CBD.

While pharmaceutical preparations can fall within the meaning of an amplifying preparation, stabilizing preparation, or balanced preparation, it will be understood that these are merely euphemistic or arbitrary categories created for the purpose of teaching general principles regarding how to manufacture a preparation designed to treat one or more particular conditions. Nevertheless, preparations may include amounts and/or ratios of cannabinoid compounds in order to have a desired balance between excitement and stabilization. In many cases the preparations may be formulated to both excite and stabilize. The relative degrees of excitement and stabilization can be selected for a specific condition or gender.

It turns out there are different strains of *Cannabis* which include differing amounts and/or ratios of the various cannibinoid compounds. For example, *Cannabis sativa* typically has a relatively high THC/CBD ratio. Conversely, *Cannabis indica* has a relative low THC/CBD ratio compared to *Cannabis sativa* (although the absolute amount of THC can be higher in *Cannabis indica* than in *Cannabis sativa*). There are also several hybrid varieties or strains of *Cannabis sativa* and *Cannabis* indica that have intermediate amounts and/or ratios of cannibinoid compounds. The amounts and/or ratios of cannibinoid compounds can change depending on the maturity of the plant, how the plant was grown, amount of artificial or natural light, climate, nutrients, and plant parts being used. In general, the buds and leaves have the highest quantities of cannibinoid compounds, while the stems and seeds have the lowest. In addition, the leaves, stems and seeds can have lower THC/CBD ratio than the buds of the same plant.

According to several embodiments, a single strain or variety of *Cannabis* can be used as the source of cannabinoid compounds in a given pharmaceutical preparation. By way of example, amplifying preparations can be made by extracting cannabinoid compounds from *Cannabis sativa* or hybrids of *Cannabis sativa* and *Cannabis* indica which are dominant toward *Cannabis sativa*. Conversely, stabilizing preparations can be made by extracting cannabinoid compounds from *Cannabis indica* or hybrids of *Cannabis sativa* and *Cannabis indica* which are more dominant toward *Cannabis indica*. Balanced preparations can be made by extracting cannabinoid compounds from hybrids of *Cannabis sativa* and *Cannabis indica* which are more balanced between THC and CBD (i.e., there is less dominance of one over the other as compared to hybrids used to make either amplifying or stabilizing preparations).

According to other embodiments, multiple strains or varieties of *Cannabis* can be used as sources of the cannabinoid compounds in a given pharmaceutical preparation. By way of example, amplifying preparations can be made by extracting cannabinoid compounds from both *Cannabis sativa* and *Cannabis indica*, wherein the quantity of *Cannabis sativa* is substantially higher. Alternatively, amplifying preparations can be made by extracting cannabinoid compounds from *Cannabis sativa* and one or more hybrids of *Cannabis sativa* and *Cannabis indica*, such as those which are dominant toward *Cannabis sativa.*

Similarly, stabilizing preparations can be made by extracting cannabinoid compounds from both *Cannabis sativa* and *Cannabis indica*, wherein the quantity of *Cannabis indica* is higher. Alternatively, amplifying preparations can be made by extracting cannabinoid compounds from *Cannabis indica* and one or more hybrids of *Cannabis sativa* and *Cannabis indica*, such as those which are dominant toward *Cannabis indica*. In addition, leaves, stems and seeds of *Cannabis sativa* can naturally have a lower THC/CBD than buds of the same plant.

Balanced preparations can be made by extracting cannabinoid compounds from both *Cannabis sativa* and *Cannabis indica*, wherein the quantities of *Cannabis indica* and *Cannabis indica* are similar. Alternatively, balanced preparations can be made by extracting cannabinoid compounds from hybrids of *Cannabis sativa* and *Cannabis indica*, such as one or more that is dominant toward *Cannabis sativa* and one or more that is dominant toward *Cannabis indica*.

Examples of *Cannabis sativa* dominant strains include Santa Maria, AK-47, Malawi gold, Bazooka, Durban Poison, Maui Waui, Early Bud, Early Pearl, Early Skunk Plant, Great White Shark, Green Spirit, Haze, Haze Skunk, Hempstar, Jack Herer, Kali Mist, Ice, LamsBread×Skunk, Leda Uno, Malawi gold, Niagra×Shiva, Night Queen, Northern Lights×Haze, Power Plant, Purple Haze, Purple Skunk, Smokey Bear, Silver Haze, Shaman, Strawberry Cough, Sweet Island Skunk, Super Silver Haze, Swazi×Skunk, Thai, Voodoo, and White Cloud.

Examples of *Cannabis indica* dominant strains include Afghani #1, Amstel Gold, Bella Caio, Big Bud, Black Domina, Black African, Black Jack, Chitral, Celtic Cross, Celtic Stone, Chronic, DoubleGum, Early Girl, Early Skunk, Eclipse, Euforia, Green Spirit, G-13, Granddaddy Purple, Hawaiian Skunk, Hindu Kush, Holland's Hope, Hypno, HashPlant, Jack Flash, K2, Lemon Stinky, Mango, Master Kush, Mazar, Mighty Might, Niagra, Northern Lights, Romulan, Pink *Indica*, Purple High, Purple Urkel, Purple Star, *Ruderalis Indica*, Shiva, Sour Bubble, Southern Afghani, Super Chrystal, and Twilight.

Examples of more balanced *sativa-indica* hybrid strains include Blueberry kush, Rainbow Kashmiri, Blue Velvet, Blueberry, BubbleBerry, Bubblegum, Buddha Plant, Cali Orange Plant, Durban Poison×Mighty Might, Flo, First Mature, Fourway #1, Fruity Pebbles, Full Moon, Jamaican Pearl, Juicy Fruit, GrapeFruit Haze, Himalayan Gold, Island Lady, KC-33, Kerala×Skunk, Kushage, Northern Berry, NYC Diesel, Purple #1, Purple Kush, Romberry, Shiva Shanti, Skunk Red Hair, Skunk Passion, Skunk Haze, Swiss Miss, Turtle Power, and White Widow.

The cannabinoid compounds can be extracted from one or more *Cannabis* plants using known methods, including organic solvent extraction, water extraction using hot or boiling water, mixed solvents using both an organic solvent and water, heat vaporization, fractional distillation, and the like. Depending on the method of extraction, the identifies and/or ratios of cannabinoid compounds can be altered or selected as desired. In general, extraction is able to provide a better approximation of the actual ratios of cannabinoid compounds found in a particular *Cannabis* plant as compared to combustion (i.e., smoking). Combustion caused significant destruction of some of the cannabinoid compounds and can change the THC/CBD ratio.

According to several embodiments, the at least one compound that enhances sexual response ("response-enhancing component") includes one or more compounds that enhance blood flow to the genital region. Examples of response-enhancing components include compounds that dilate blood vessels, such as compounds that increase the amount of nitric oxide (NO) in the blood. These include known pharmaceutical drugs as well as herbal supplements that have been shown to enhance sexual response and improve performance. The response-enhancing component can address ED in men and/or physical problems in women that can inhibit or delay performance, whether from a physical or psychological standpoint.

Specific examples of response-enhancing components include sildenafil (Viagra®), tadalifil (Cialis®), vardenafil (Levitra®), and herbal supplements such as L-arginine, Yahimbe Root, Vigorplex®, Tongkat Ali Extract, Libidus, Maxidus, Xzen XPress, Xzen Gold, Xzen Platinum, Xzen 1200, WOW, Zytenz, Vydexafil, Libido Boost Plus, AI Sports Perform, OxyErect Pro, Noxysurge, VitalKoR, Athletic Edge APE, Axcite Magnum, VirMax, Virilis Pro, Virility-X, XZone, Silver Sword, Stiff Nights, Wood-E, Nite Rider, Royal Dragon Herbal Tonic Balls, Reload, Super Cheetah, Cave Diver, Mojo Risen, Lightning Rod, Zoom-Zooma-Zoom, Love Rider, Ninja Mojo, Rock-it Man, Mojo Nights, EreXite, VMaxx Rx, Firminite, Instant Rock Hard, ZenMaxx, Black Ant, RigiRx Plus, France T253, African Black Ant, Man King, ViaXtreme, Man Up, Herbal Vigor Quick Fix, Arize, O.M.G., Gold Vigra, Miraculous Evil Root, Zhen Gong Fu, GoldReallas, Full Throttle On Demand, 3 Hard Knights, Eyeful, Liu Bian Li, MV5 Days, S.W.A.G., Weekend Warrior, Bali Mojo, Jinquiangbudor Red Dragon, Vimax, Tiger King, SexRx, Best Whips, CONTROL, Alpha Male, ExtenZe, Vitalikor Fast Acting, Clalis, Exten 1300, MVP Mega, MaxTreme Zen, Get It Up, Nights To Remember, Bullet Proof, Vicerex, Sex Plus, Affirm XL, Libido Sexual Enhancer, Kaboom Action Strips, and X-Rock. The amount of such component(s) can vary depending on the potency and mode of action. In general, such compounds enable men to achieve and maintain an erection by increasing blood flow to the genital region. For reasons that may not be well-understood, they also aid women when combined with cannabinoid compounds as disclosed herein, which is a surprising and unexpected result (i.e., since they typically have no effect on women when used alone).

While enabling sexual activity can, by itself, increase sexual pleasure, response-enhancing components do not enhance sexual pleasure per se (e.g., in a perfectly healthy man who does not suffer from erectile dysfunction, the use of response-enhancing drugs does not significantly affect the pleasure of the sexual act, including climax). They may simply provide the fun and novelty of longer-lasting and/or quicker threshold erections. Similarly, while cannabinoids can make a person "high" and therefore more relaxed and uninhibited, they are also known to diminish sexual response and performance, particularly in men. In some cases, they can prevent achieving or maintaining an erection. In other cases, they can unnecessarily prolong or prevent climax. Unexpectedly, however, it has now been found that combining one or more response-enhancing components with one or more pleasure-enhancing components optimizes the beneficial effects of both while offsetting or eliminating the negative effects. This greatly enhances the overall sexual experience.

Even more unexpectedly, combining one or more response-enhancing components with one or more pleasure-enhancing components can provide the elusive aphrodisiac (or "Spanish fly") that has been the subject of myth and lore but not actually achieved in reality. Unlike men, in which sexual activity is predominately (and logistically) physical and secondarily psychological, women can technically engage in sexual activity whether or not they care to or are the least bit aroused. As such, sexual pleasure is more complicated in women and is as much or more psychological as it is physical. For this reason, in both humans and animals, sexual activity is typically initiated by males rather than females. The pharmaceutical preparations disclosed herein can shift this balance and give women more initial threshold desire as well as actual sexual pleasure, which inure to the benefit of both women and their sexual partners. Without being bound to any particular theory, it is postulated that increasing blood flow to the genital region of women, while not itself having been proven to improve either sexual pleasure or sexual response, increases the effects of the cannabinoid compounds, both physically and psychologically so that, when used together, they synergistically act together to provide increased sexual pleasure and response as compared to when using either alone.

Additional supplements that can improve sexual pleasure and/or response in men and women include ginseng, ginseng, ginko biloba, yohimbe, and horny goat weed.

The pharmaceutical preparations can have a variety of different modes of delivery, which can be gender-specific or otherwise tailored for the specific needs or desires of the patient. According to an embodiment, the pharmaceutical preparation can be designed as a topical (e.g., massage oils, scented lotions, gels, creams, lubricants, vaginal patch). Alternatively or in addition, they can be formulated for ingestion (e.g., oral drops, capsules, tablets, and food preparations). Alternatively, they can be formulated for inhalation (e.g., by a vaporizer). In general, extraction of cannabinoids and then delivery without combustion can provide superior results compared to smoking weed and ingesting an ED drug. Combustion destroys a significant quantity of cannabinoid compounds and can change their ratios, which makes proper dosing difficult. Smoking weed and ingesting an ED drug also suffers from the inability to control the timing of each, since smoking causes almost instantaneous high while ingesting an ED drug takes time for the body to metabolize. The result can be premature cannabinoid effect, with delayed blood-flow increasing effect coupled with reduced cannabinoid effect when it is desirable for both to be maximized. Delivering both the pleasure-enhancing and performance-enhancing components in a single preparation and/or in the same manner can better control dosing and timing.

EXAMPLES

For purposes of the following examples, sexual pleasure and sexual response are assigned a value of 5 on a scale of 1 to 10, with 1 being the lowest and 10 being the highest. Three categories in men were measured: hardness of erection on a scale of 1 to 10; sensitivity on a scale of 1 to 10; and strength of orgasm on a scale of 1 to 10. Three categories in women are measured: threshold desire on a scale of 1 to 10; sensitivity on a scale of 1 to 10; and strength of orgasm on a scale of 1 to 10.

Example 1

The subject was a 41 year old male. The marijuana strain used to provide the cannabinoid compounds was AK-47 hybrid strain. The marijuana was delivered orally usable an edible. The marijuana plant parts (mostly leaves and buds) were ground up and simmered in vegetable oil for 3 hours to extract cannabinoid compounds and then strained. The cannabinoid infused oil was assumed to contain roughly the same ratio of THC to CBD in the plant parts (as well as other cannabinoids in the plant parts).

The infused oil was used in place of the oil called for in normal preparation of brownies per instructions. The cannabinoid infused oil was blended in an amount of ¼ ounce per 18 ounce fudge brownie mix. Brownies containing the extracted cannabinoid compounds were prepared from the mixed batter by placing into a small cake pan (6 in$^2$) and baked in the over according to instructions. A small pan of brownies was cut up into 3 in squares.

The subject ingested two brownies and one XZEN pill. The subject started noticing the effects of both after about 1 hour and commenced sexual activity with a female partner shortly thereafter. The subject was able to obtain and maintain a hard erection and sensitivity and pleasure during sex were increased. The subject was able to last longer than usual and, in this case, sex lasted about 30 minutes. At the culmination, ejaculation was very intense. The statistics were (on a scale of 1 to 10): hardness of erection: 9; sensitivity: 8; strength of orgasm: 10.

The female partner weighed less than the male subject and ingested one cannabinoid infused brownie square and also experienced heightened sensitivity (8) and pleasure during the sexual activity, which was attributed to reduced anxiety and inhibition and increased threshold desire. The female did not ingest any blood flow enhancements. It is postulated that the female partner would further benefit from combining ingestion of the cannabinoid edible with a component that increases blood flow to the female genital region in order to increase threshold desire (e.g., 8 as a result of swelling and thickening of the clitoris and labia), as well as more intense orgasm (e.g., 8) as a result of the combined psychological and physiological effects of ingesting both the pleasure-enhancing and performance-enhancing component.

Example 2

The subject was a 70 year old male. The marijuana strain used to provide the cannabinoid compounds was AK-47. The cannabinoid compounds were extracted by simmering ¼ ounce of marijuana in 1 cup avocado oil to make butter. The subject spread approximately 1 tablespoon of the butter onto toast and then ingested the toast and one XZEN pill on an empty stomach. After 45 minutes the subject felt some flushing and effects of the cannabinoid compounds.

After one hour the subject had a hard erection and proceeded to have sex with a female partner of similar age. The sex lasted an amazing 2 hours and the subject was able to ejaculate 5 times within that time span, which would be remarkable for a young but in this case the subject was a 70 year old man. The statistics were (on a scale of 1 to 10): hardness of erection: 10; sensitivity: 9; strength of orgasm: 9. This example exemplifies the benefit to an older man of using cannabinoids with a higher ratio of THC:CBD (at least 2:1). The subject's opinion was that the sex was like being a young man all over again ("21 again"), and his overall mood in general improved dramatically (demeanor and disposition), which was another unexpected benefit.

The female partner did not ingest any enhancements. However, it is postulated that the female partner would benefit from ingesting the preparations disclosed herein and experience increased threshold desire (8), heightened sensitivity and pleasure (8), and more powerful orgasm (8).

Example 3

The subject was a 41 year old male. The marijuana strain used to provide the cannabinoid compounds was Blueberry kush. The marijuana was delivered orally usable an edible. The marijuana plant parts (mostly leaves and buds) were ground up and simmered in vegetable oil for 3 hours to extract cannabinoid compounds and then strained. The cannabinoid infused oil was assumed to contain roughly the same ratio of THC to CBD in the plant parts (as well as other cannabinoids in the plant parts).

The infused oil was used in place of the oil called for in normal preparation of brownies per instructions. The cannabinoid infused oil was blended in an amount of ¼ ounce per 18 ounce fudge brownie mix. Brownies containing the extracted cannabinoid compounds were prepared from the mixed batter by placing into a small cake pan (6 in$^2$) and baked in the over according to instructions. A small pan of brownies was cut up into 3 in squares.

The subject ingested two brownies and one XZen pill. The subject started noticing the effects of both after about 1 hour and commenced sexual activity shortly thereafter. The subject was able to maintain a hard erection and sensitivity was increased. The subject was able to last longer and sex lasted about 45 minutes with a female partner. Ejaculation was very intense. The subject was thereafter able to achieve another erection after 30 minutes and commenced sexual activity again, which lasted about 30 minutes, and able to achieve a second orgasm. The statistics were (on a scale of 1 to 10): hardness of erection: 9; sensitivity: 8; strength of orgasm: 9. This example, as compared to Example 1, demonstrates the beneficial effects for a relatively young, healthy man when using a cannabinoid having a more balanced ratio of THC to CBD (which was closer to 1:1 than in Example 1 and possibly less 1:1), relative to the ability to last longer.

The female partner ingested one cannabinoid infused brownie square and also experienced heightened sensitivity and pleasure (8) during the sexual activity, which was attributed to reduced anxiety and inhibition and increased threshold desire. The female did not ingest any blood flow enhancements. It is postulated that the female partner would further benefit from combining ingestion of the cannabinoid edible with a component that increases blood flow to the female genital region in order to increase threshold desire (e.g., 8 as a result of swelling and thickening of the clitoris and labia), as well as more intense orgasm (8) as a result of the combined psychological and physiological effects of ingesting both the pleasure-enhancing and performance-enhancing component.

Example 4

The subject was a 70 year old male. The marijuana strain used to provide the cannabinoid compounds was Blueberry kush. The cannabinoid compounds were extracted by simmering ¼ ounce of marijuana in 1 cup avocado oil to make butter. The subject spread approximately 1 tablespoon of the butter onto toast and then ingested the toast and one XZEN pill on an empty stomach. After 45 minutes the subject felt some flushing and effects of the cannabinoid compounds.

After one hour the subject had a hard erection and proceeded to have sex with a female partner of similar age. The sex lasted 2 hours and the subject was able to ejaculate 3 times within that time span. The statistics were (on a scale of 1 to 10): hardness of erection: 10; sensitivity: 9; strength of orgasm: 9. This example demonstrated that while a clear benefit was obtained by the subject ingesting a balanced ratio of THC:CBD, the results were not quite as dramatic as Example 2, in which the subject ingested a higher ratio of THC:CBD and was able to achieve 5 orgasms instead of 3.

The female partner did not ingest any enhancements. However, it is postulated that the female partner would benefit from ingesting the preparations disclosed herein and experience increased threshold desire (8), heightened sensitivity and pleasure (8), and more powerful orgasm (8).

Example 5

A 50 year old male ingested a single brownie prepared according to Example 3 and one XZen pill. The subject felt the effects of both components and was able to achieve an erection more quickly and maintain it longer. The subject engaged in sexual activities with a female partner within about 1-2 hours of ingestion lasting about 30 minutes. The subject had an erection of about an 8, heightened sensitivity of about 8; and a more intense orgasm of about 8. It is postulated that the male subject might have benefited more using the higher THC:CBD preparation and/or ingesting an increased quantity of the edible.

The female partner did not ingest any enhancements. However, it is postulated that the female partner would benefit from ingesting the preparations disclosed herein and experience increased threshold desire (8), heightened sensitivity and pleasure (8), and more powerful orgasm (8).

Example 6

The subject is a 22 year old male who is provided with an infused edible made according to any of the foregoing Examples. The subject is strong and virile but prone to premature ejaculation. The subject ingests the infused edible together with a component that increases bloodflow to the genital region (e.g., XZen for Women or part of a Viagra®). After 20-30 minutes the subject has a hard erection and proceeds to have sex with a partner. When using an edible with high THC:CBD ratio, the sex is brief (about 1-3 minutes) but intense. The statistics are (on a scale of 1 to 10): hardness of erection: 10; sensitivity: 8; strength of orgasm: 8.

Alternatively, the subject ingests a cannabinoid infused edible having a higher ratio of CBD:THC and experiences the same quality of erection, sensitivity, and strength of orgasm but is able to last much longer than usual (e.g., 15-45 minutes), which greatly boosts the subject's confidence when engaging in sexual activities with others. Due to the subject's age, he is able to achieve multiple orgasms with fast or immediate recovery between ejaculations.

This example demonstrates that, while a clear benefit was obtained by the subject ingesting a high ratio of THC:CBD, the results were objectively much better when the subject ingests a much lower ratio of THC:CBD (or higher ratio of CBD:THC). It is postulated that a more balanced ratio of THC:CBD would provide an intermediate benefit between the extremes described herein.

Example 7

The subject is a 21 year old female who is provided with an infused edible made according to any of the foregoing Examples. The subject is healthy but inexperienced and nervous when engaging in sexual activity, which decreases threshold desire, pleasure and fulfillment, and makes it difficult or impossible for the subject to achieve orgasm. The subject ingests the infused edible together with a component that increases bloodflow to the genital region (e.g., XZen for Women or part of a Viagra®). After about 1 hour the subject feels flushing and the effects of the cannabinoid compounds, including increased swelling of the vulva and nipples which, although largely physiological, combine with the enhanced psychological effects of excitement and decreased anxiety provided by the infused edible to increase threshold desire (e.g., 9).

When the subject ingests an edible containing a high THC:CBD ratio, the subject may be more physically aggressive but might still have difficulty achieving orgasm regularly. It is postulated that a higher CBD:THC ratio would provide a calming effect that permits more deep psychological appreciation and enjoyment of sexual activity, leading to more reliable and fulfilling orgasms. Depending on the woman, an intermediate TCD:CBD ratio may be sufficiently calming, yet more excitatory so as to promote quicker and/or multiple orgasms.

Example 8

A 25 year old female subject is provided with an infused edible made according to any of the foregoing Examples. The subject ingests the infused edible together with a component that increases bloodflow to the genital region (e.g., XZen for Women or part of a Viagra®). After about 1 hour the subject feels flushing and the effects of the cannabinoid compounds, including increased swelling of the vulva and nipples which, although largely physiological, combine with the enhanced psychological effects of excitement and decreased anxiety provided by the infused edible to increase threshold desire.

After one hour the subject commences sexual activity with a 41 year old male partner. The subject experiences heightened sensitivity (9) and pleasure and is able to climax more quickly and more powerfully (9) than usual. Depending on the endurance of her male sex partner, the female subject is able to achieve multiple orgasms as a result of the increased physiological and psychological awareness and sensitivities provided by the combined use of pleasure-enhancing and performance-enhancing components. Because of the female subject's age (25) and sexual confidence, it is postulated that the subject would, like the 41 year old subject of Examples 1 and 3, benefit from an edible having a balanced THC:CBD ratio.

Example 9

A 68 year old female subject of normal sexual experience and activity for her age is provided with an infused edible made according to any of the foregoing Examples. The subject ingests the infused edible together with a component that increases bloodflow to the genital region (e.g., XZen for Women or part of a Viagra®). After about 1 hour the subject feels flushing and the effects of the cannabinoid compounds, including increased swelling of the vulva and nipples which, although largely physiological, combine with the enhanced psychological effects of excitement and decreased anxiety provided by the infused edible to increase threshold desire.

After one hour the subject commences sexual activity with a male partner of similar age. The subject experiences high threshold desire (7), heightened sensitivity (9) and is able to climax more quickly and more powerfully (9) than usual. Depending on the endurance of her male sex partner, the female subject is able to achieve multiple orgasms as a result of the increased physiological and psychological awareness and sensitivities provided by the combined use of pleasure-enhancing and performance-enhancing components. Because of the female subject's age (68), it is postulated that the subject would, like the 70 year old subject of Examples 2 and 4, benefit more from an edible having a higher THC:CBD ratio.

Example 10

A 45 year old female subject is provided with an infused edible made according to any of the foregoing Examples. The subject ingests the infused edible together with a component that increases bloodflow to the genital region (e.g., XZen for Women or part of a Viagra®). After about 1 hour the subject feels flushing and the effects of the cannabinoid compounds, including increased swelling of the vulva and nipples which, although largely physiological, combine with the enhanced psychological effects of excitement and decreased anxiety provided by the infused edible to increase threshold desire (9).

After one hour the subject commences sexual activity with a male partner of similar age. The subject experiences heightened sensitivity (9) and pleasure and is able to climax more quickly and more powerfully (9) than usual. Depending on the endurance of her male sex partner, the female subject is able to achieve multiple orgasms as a result of the increased physiological and psychological awareness and sensitivities provided by the combined use of pleasure-enhancing and performance-enhancing components. Because of the female subject's age (45), it is postulated that the subject would, like the 50 year old subject of Example 5, benefit more from an edible having a higher THC:CBD ratio and/or ingesting a higher quantity of edible having a balanced THC:CBD ratio.

Example 11

A 70 year old female subject who rarely engages in sexual activity because of lost desire and pleasure is provided with an infused edible made according to any of the foregoing Examples. The subject ingests the infused edible together with a component that increases bloodflow to the genital region (e.g., XZen for Women or part of a Viagra®). After about 1 hour the subject feels flushing and the effects of the cannabinoid compounds, including increased swelling of the vulva and nipples which, although largely physiological, combine with the enhanced psychological effects of excitement and decreased anxiety provided by the infused edible to increase threshold desire (7 or 8).

After one hour the subject commences sexual activity with a male partner of similar age. The subject experiences heightened sensitivity (7 or 8) and pleasure and is able to achieve climax (6 or 7), perhaps for the first time in a long time or ever. Depending on the endurance of her male sex partner, the female subject is able to achieve multiple orgasms as a result of the increased physiological and psychological awareness and sensitivities provided by the combined use of pleasure-enhancing and performance-enhancing components. Because of the female subject's age (70), it is postulated that the subject might, like the 70 year old subject of Examples 2 and 4, benefit more from an edible having a higher THC:CBD ratio.

Example 12

Any of the foregoing examples is modified by providing at least one of the components (e.g., pleasure-enhancing component) in a topical preparation that can delivered by inhalation. Examples include, for example, vaporizers heats one or more components of the pharmaceutical preparation with water to provide a vapor that carries the components of interest and can be inhaled. The temperature and/or selection of vaporizing liquids can affect the concentration and/or ratio of cannabinoids delivered to the user.

Example 13

Any of the foregoing examples is modified by providing at least one of the components (e.g., pleasure-enhancing component) in a topical preparation that can be applied to any region of the body able to rapidly absorb the active components. Examples include, for example, the genital and/or anal regions of men and women.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tablet or capsule for enhancing sexual response and sensitivity in a human, consisting essentially of:
   a *cannabis* extract consisting essentially of about 50 mg to about 500 mg of tetrahydrocannabinol (THC) and about 10 mg to about 250 mg of cannabidiol (CBD); and a pharmaceutically effective amount of a component selected from the group consisting of sildenafil, tadalafil, and vardenafil.

2. The tablet or capsule of claim 1, wherein the *cannabis* extract contains at least one of cannabinol (CBN), tetrahydrocannabivarin (THCV), cannabigerol (CBG), dronabinol, nabilone, a derivative of THC, or a derivative of CBD.

3. The tablet or capsule of claim 1, wherein the *cannabis* extract is obtained from plant parts of one or more plants selected from *Cannabis sativa, Cannabis indica*, and hybrids thereof.

4. The tablet or capsule of claim 1, wherein the tablet or capsule contains about 75 mg to about 400 mg of THC.

5. The tablet or capsule of claim 1, wherein the tablet or capsule contains about 100 mg to about 300 mg of THC.

6. The tablet or capsule of claim 1, wherein the tablet or capsule contains about 75 mg to about 400 mg of THC and about 15 mg to about 200 mg of CBD.

7. The tablet or capsule of claim 1, wherein the tablet or capsule contains ratio of THC to CDB of at least about 2:1 THC/CBD.

8. The tablet or capsule of claim 7, wherein the ratio of THC to CDB is in a range of about 3:1 to about 20:1 THC/CBD.

9. The tablet or capsule of claim 7, wherein the ratio of THC to CDB is in a range of about 4:1 to about 15:1 THC/CBD.

10. The tablet or capsule of claim 1, wherein the tablet or capsule consists essentially of the *cannabis* extract and vardenafil.

11. A tablet or capsule for enhancing sexual response and sensitivity in a human, consisting essentially of:
   a *cannabis* extract consisting essentially of about 50 mg to about 500 mg of tetrahydrocannabinol (THC) and about 10 mg to about 250 mg of cannabidiol (CBD); and
   a pharmaceutically effective amount of sildenafil.

12. The tablet or capsule of claim 11, wherein the *cannabis* extract contains at least one of cannabinol (CBN), tetrahydrocannabivarin (THCV), cannabigerol (CBG), dronabinol, nabilone, a derivative of THC, or a derivative of CBD.

13. The tablet or capsule of claim 11, wherein the tablet or capsule has a ratio of THC to CDB in a range of about 2:1 to about 25:1 THC/CBD.

14. The tablet or capsule of claim 13, wherein the ratio of THC to CDB is in a range of about 3:1 to about 20:1 THC/CBD.

15. The tablet or capsule of claim 13, wherein the ratio of THC to CDB is in a range of about 4:1 to about 15:1 THC/CBD.

16. A tablet or capsule for enhancing sexual response and sensitivity in a human, consisting essentially of:
   a *cannabis* extract consisting essentially of about 50 mg to about 500 mg of tetrahydrocannabinol (THC) and about 10 mg to about 250 mg of cannabidiol (CBD); and
   a pharmaceutically effective amount of tadalafil.

17. The tablet or capsule of claim 16, wherein the *cannabis* extract contains at least one of cannabinol (CBN), tetrahydrocannabivarin (THCV), cannabigerol (CBG), dronabinol, nabilone, a derivative of THC, or a derivative of CBD.

18. The tablet or capsule of claim 16, wherein the tablet or capsule has a ratio of THC to CDB in a range of about 2:1 to about 25:1 THC/CBD.

19. The tablet or capsule of claim 18, wherein the ratio of THC to CDB is in a range of about 3:1 to about 20:1 THC/CBD.

20. The tablet or capsule of claim 18, wherein the ratio of THC to CDB is in a range of about 4:1 to about 15:1 THC/CBD.

\* \* \* \* \*